US009622739B2

(12) United States Patent
Dreyfuss et al.

(10) Patent No.: US 9,622,739 B2
(45) Date of Patent: *Apr. 18, 2017

(54) SUTURE ANCHOR

(71) Applicant: Arthrex, Inc., Naples, FL (US)

(72) Inventors: Peter J. Dreyfuss, Naples, FL (US); William C. Benavitz, Naples, FL (US)

(73) Assignee: Arthrex, Inc., Naples, FL (US)

( * ) Notice: Subject to any disclaimer, the term of this patent is extended or adjusted under 35 U.S.C. 154(b) by 304 days.

This patent is subject to a terminal disclaimer.

(21) Appl. No.: 14/487,459

(22) Filed: Sep. 16, 2014

(65) Prior Publication Data

US 2015/0005819 A1 Jan. 1, 2015

Related U.S. Application Data

(63) Continuation of application No. 14/155,556, filed on Jan. 15, 2014, now abandoned, which is a
(Continued)

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0414* (2013.01); *Y10T 29/49947* (2015.01)

(58) Field of Classification Search
CPC ........ A61B 17/0401; A61B 2017/0414; A61B 2017/044; A61B 2017/0409; A61B 2017/0446; A61B 2017/0448
See application file for complete search history.

(56) References Cited

U.S. PATENT DOCUMENTS 74,489 A 2/1868 Bidwell
85,794 A 1/1869 Crosby
(Continued)

FOREIGN PATENT DOCUMENTS

CA 2045903 6/1991
EP 0465910 A1 1/1992
(Continued)

OTHER PUBLICATIONS

Apreleva, Ph.D. et al., Maria, Rotator Cuff Tears: The Effect of the Reconstruction Method on Three-Dimensional Repair Site Area, Arthroscopy: The Journal of Arthroscopic and Related Surgery, vol. 18, No. 5 May-Jun. 2002: pp. 519-526.
(Continued)

*Primary Examiner* — Dianne Dornbusch
(74) *Attorney, Agent, or Firm* — Carlson, Gaskey & Olds, P.C.

(57) ABSTRACT

A suture anchor assembly includes an anchor body having a central longitudinal axis, a proximal end, a distal end, a passage extending along the central longitudinal axis from an opening at the proximal end through a portion of a length of the anchor body, and a helical thread that defines a perimeter the proximal end of the anchor body. The passage has a first wall portion and a second wall portion. A rigid support extends across the passage and has a first portion and a second portion spaced from the first portion. The first portion is attached to the first wall portion and the second portion is attached to the second wall portion. A suture strand having a suture length is threaded into the passage, supported by the rigid support, and threaded past the proximal end of the anchor body. The rigid support is spaced axially away from the opening, and the suture strand extends out of the opening of the anchor body. A driver includes a shaft having a shaft length that engages the anchor body, and
(Continued)

the suture length of the at least one suture strand is greater than the shaft length of the shaft.

35 Claims, 4 Drawing Sheets

Related U.S. Application Data continuation of application No. 14/148,460, filed on Jan. 6, 2014, now Pat. No. 8,801,755, which is a continuation of application No. 13/933,575, filed on Jul. 2, 2013, now Pat. No. 8,623,052, which is a continuation of application No. 12/751,266, filed on Mar. 31, 2010, now abandoned, which is a continuation of application No. 11/097,172, filed on Apr. 4, 2005, now Pat. No. 8,343,186.

(60) Provisional application No. 60/559,425, filed on Apr. 6, 2004.

(56) References Cited

U.S. PATENT DOCUMENTS

| | | |
|---|---|---|
| 176,335 A | 4/1876 | Morton |
| 463,650 A | 11/1891 | Stevens |
| 1,379,606 A | 5/1921 | Ashley |
| 1,574,578 A | 2/1926 | Holmes |
| 1,610,309 A | 12/1926 | Niederer |
| 1,925,174 A | 9/1933 | Creamean |
| 2,045,903 A | 6/1936 | Fortin |
| 2,121,193 A | 6/1938 | Hanicke |
| 2,243,717 A | 5/1941 | Moreira |
| 2,329,398 A | 9/1943 | Duffy |
| 2,381,050 A | 8/1945 | Hardinge |
| 2,397,216 A | 3/1946 | Stellin |
| 2,490,364 A | 2/1948 | Livingston |
| 2,472,103 A | 6/1949 | Giesen |
| 2,489,870 A | 11/1949 | Dzus |
| 2,562,419 A | 7/1951 | Ferris |
| 2,570,465 A | 10/1951 | Lundholm |
| 2,699,774 A | 1/1955 | Livingston |
| 2,787,186 A | 4/1957 | Brogiotti |
| 2,817,339 A | 12/1957 | Sullivan |
| 2,890,734 A | 6/1959 | Mullin |
| 3,143,916 A | 8/1964 | Rice |
| 3,420,929 A | 1/1969 | Morin |
| 3,575,080 A | 4/1971 | Hannay |
| 3,579,831 A | 5/1971 | Stevens |
| 3,584,667 A | 6/1971 | Reiland |
| 3,664,400 A | 5/1972 | Moore |
| 3,716,058 A | 2/1973 | Tanner, Jr. |
| 3,768,635 A | 10/1973 | Eggert |
| 3,842,825 A | 10/1974 | Wagner |
| 3,861,269 A | 1/1975 | Laverty |
| 3,910,281 A | 10/1975 | Kletschka et al. |
| 3,910,282 A | 10/1975 | Messer et al. |
| 3,951,261 A | 4/1976 | Mandel et al. |
| 3,990,438 A | 11/1976 | Pritchard |
| 4,006,657 A | 2/1977 | Dunnette |
| 4,006,747 A | 2/1977 | Kronenthal et al. |
| 4,013,071 A | 3/1977 | Rosenberg |
| 4,041,939 A | 8/1977 | Hall |
| 4,114,508 A | 9/1978 | Jeal |
| 4,135,623 A | 1/1979 | Thyen |
| 4,175,555 A | 11/1979 | Herbert |
| 4,222,689 A | 9/1980 | Fujiwara |
| 4,241,638 A | 12/1980 | Shimizu et al. |
| 4,244,370 A | 1/1981 | Furlow et al. |
| 4,250,674 A | 2/1981 | Feist |
| 4,275,717 A | 6/1981 | Bolesky |
| 4,289,124 A | 9/1981 | Zickel |
| 4,301,551 A | 11/1981 | Dore et al. |
| 4,329,099 A | 5/1982 | Shimizu et al. |
| 4,351,069 A | 9/1982 | Ballintyn et al. |
| 4,406,623 A | 9/1983 | Grafelmann et al. |
| 4,419,029 A | 12/1983 | Wenzel |
| 4,424,898 A | 1/1984 | Thyen et al. |
| 4,454,875 A | 6/1984 | Pratt et al. |
| 4,467,478 A | 8/1984 | Jurgutis |
| 4,468,200 A | 8/1984 | Munch |
| 4,483,023 A | 11/1984 | Hoffman, Jr. et al. |
| 4,507,817 A | 4/1985 | Staffeld |
| 4,519,100 A | 5/1985 | Wills et al. |
| 4,520,511 A | 6/1985 | Gianezio et al. |
| 4,537,185 A | 8/1985 | Stednitz |
| 4,539,981 A | 9/1985 | Tunc |
| 4,569,338 A | 2/1986 | Edwards |
| 4,590,928 A | 5/1986 | Hunt et al. |
| 4,597,776 A | 7/1986 | Ullman et al. |
| 4,601,625 A | 7/1986 | Ernst et al. |
| 4,605,414 A | 8/1986 | Czajka |
| 4,611,580 A | 9/1986 | Wu |
| 4,632,100 A | 12/1986 | Somers et al. |
| 4,633,869 A | 1/1987 | Schmieding |
| 4,640,271 A | 2/1987 | Lower |
| 4,672,957 A | 6/1987 | Hourahane |
| 4,693,654 A | 9/1987 | Bettini |
| 4,712,542 A | 12/1987 | Daniel et al. |
| 4,723,541 A | 2/1988 | Reese |
| 4,738,255 A | 4/1988 | Goble et al. |
| 4,741,330 A | 5/1988 | Hayhurst |
| 4,750,492 A | 6/1988 | Jacobs |
| 4,756,653 A | 7/1988 | Berger |
| 4,784,126 A | 11/1988 | Hourahane |
| 4,815,467 A | 3/1989 | Chestnut |
| 4,870,957 A | 10/1989 | Goble et al. |
| 4,892,429 A | 1/1990 | Giannuzzi |
| 4,898,156 A | 2/1990 | Gatturna et al. |
| 4,946,467 A | 8/1990 | Ohi et al. |
| 4,946,468 A | 8/1990 | Li |
| 4,963,144 A | 10/1990 | Huene |
| 4,976,715 A | 12/1990 | Bays et al. |
| 4,978,350 A | 12/1990 | Wagenknecht |
| 4,988,351 A | 1/1991 | Paulos et al. |
| 5,002,550 A | 3/1991 | Li |
| 5,002,563 A | 3/1991 | Pyka et al. |
| 5,019,079 A | 5/1991 | Ross |
| 5,037,422 A | 8/1991 | Hayhurst et al. |
| 5,041,129 A | 8/1991 | Hayhurst et al. |
| 5,047,030 A | 9/1991 | Draenert |
| 5,059,077 A | 10/1991 | Schmid |
| 5,059,201 A | 10/1991 | Asnis |
| 5,061,181 A | 10/1991 | Niznick |
| 5,067,956 A | 11/1991 | Buford, III et al. |
| 5,074,790 A | 12/1991 | Bauer |
| 5,084,050 A | 1/1992 | Draenert |
| 5,087,201 A | 2/1992 | Mondani et al. |
| 5,100,417 A | 3/1992 | Cerier et al. |
| 5,100,471 A | 3/1992 | Winnik et al. |
| 5,102,414 A | 4/1992 | Kirsch |
| 5,102,421 A | 4/1992 | Anspach, Jr. |
| 5,108,397 A | 4/1992 | White |
| 5,116,178 A | 5/1992 | Lerman et al. |
| 5,120,171 A | 6/1992 | Lasner |
| 5,120,172 A | 6/1992 | Wakai |
| 5,129,901 A | 7/1992 | Decoste |
| 5,139,499 A | 8/1992 | Small et al. |
| 5,139,520 A | 8/1992 | Rosenberg |
| 5,141,520 A | 8/1992 | Goble et al. |
| D330,591 S | 10/1992 | Rosenberg et al. |
| 5,152,790 A | 10/1992 | Rosenberg et al. |
| 5,156,616 A | 10/1992 | Meadows et al. |
| 5,163,960 A | 11/1992 | Bonutti |
| D331,463 S | 12/1992 | Rosenberg et al. |
| 5,176,682 A | 1/1993 | Chow |
| 5,180,382 A | 1/1993 | Frigg et al. |
| 5,205,746 A | 4/1993 | Chanavaz |
| 5,207,679 A | 5/1993 | Li |
| 5,211,647 A | 5/1993 | Schmieding |
| 5,217,486 A | 6/1993 | Rice et al. |
| 5,224,946 A | 7/1993 | Hayhurst et al. |
| 5,236,445 A | 8/1993 | Hayhurst et al. |
| 5,242,447 A | 9/1993 | Borzone |

(56) References Cited

U.S. PATENT DOCUMENTS

| | | |
|---|---|---|
| 5,246,369 A | 9/1993 | Poulmaire |
| 5,246,441 A | 9/1993 | Ross et al. |
| 5,250,055 A | 10/1993 | Moore et al. |
| 5,258,016 A | 11/1993 | DiPoto et al. |
| 5,261,914 A | 11/1993 | Warren |
| 5,268,001 A | 12/1993 | Nicholson et al. |
| 5,275,176 A | 1/1994 | Chandler |
| 5,285,016 A | 2/1994 | Narizuka et al. |
| 5,306,290 A | 4/1994 | Martins et al. |
| 5,312,412 A | 5/1994 | Whipple |
| 5,312,438 A | 5/1994 | Johnson |
| 5,320,626 A | 6/1994 | Schmieding |
| 5,324,308 A | 6/1994 | Pierce |
| 5,326,205 A | 7/1994 | Anspach, Jr. et al. |
| 5,327,896 A | 7/1994 | Schmieding |
| 5,330,468 A | 7/1994 | Burkhart |
| 5,334,204 A | 8/1994 | Clewett et al. |
| 5,336,240 A | 8/1994 | Metzler et al. |
| 5,350,383 A | 9/1994 | Schmieding et al. |
| 5,354,298 A | 10/1994 | Lee et al. |
| 5,356,413 A | 10/1994 | Martins et al. |
| 5,356,435 A | 10/1994 | Thein |
| 5,360,448 A | 11/1994 | Thramann |
| 5,364,400 A | 11/1994 | Rego, Jr. et al. |
| 5,370,661 A | 12/1994 | Branch |
| 5,370,662 A | 12/1994 | Stone et al. |
| 5,375,956 A | 12/1994 | Pennig |
| 5,376,119 A | 12/1994 | Zimmermann et al. |
| 5,380,334 A | 1/1995 | Torrie et al. |
| 5,383,905 A | 1/1995 | Golds et al. |
| D357,534 S | 4/1995 | Hayes |
| 5,403,136 A | 4/1995 | Mathys |
| 5,411,506 A | 5/1995 | Goble et al. |
| 5,411,523 A | 5/1995 | Goble |
| 5,414,966 A | 5/1995 | Montoya |
| 5,417,533 A | 5/1995 | Lasner |
| 5,417,691 A | 5/1995 | Hayhurst |
| 5,417,712 A | 5/1995 | Whittaker et al. |
| D359,557 S | 6/1995 | Hayes |
| 5,423,860 A | 6/1995 | Lizardi et al. |
| 5,441,502 A | 8/1995 | Bartlett |
| 5,441,508 A | 8/1995 | Gazielly et al. |
| 5,443,482 A | 8/1995 | Stone et al. |
| 5,447,401 A | 9/1995 | Jones et al. |
| 5,451,225 A | 9/1995 | Ross, Jr. et al. |
| 5,456,267 A | 10/1995 | Stark |
| 5,456,685 A | 10/1995 | Huebner |
| 5,458,602 A | 10/1995 | Goble et al. |
| 5,458,608 A | 10/1995 | Wortrich |
| 5,462,644 A | 10/1995 | Woodson |
| 5,464,425 A | 11/1995 | Skiba |
| 5,464,427 A | 11/1995 | Curtis et al. |
| 5,466,243 A | 11/1995 | Schmieding et al. |
| 5,470,334 A | 11/1995 | Ross et al. |
| 5,480,403 A | 1/1996 | Lee et al. |
| 5,486,197 A | 1/1996 | Le et al. |
| 5,489,210 A | 2/1996 | Hanosh |
| 5,492,442 A | 2/1996 | Lasner |
| 5,496,326 A | 3/1996 | Johnson |
| 5,501,695 A | 3/1996 | Anspach, Jr. et al. |
| 5,501,696 A | 3/1996 | Trott |
| 5,505,735 A | 4/1996 | Li |
| 5,505,736 A | 4/1996 | Reimels et al. |
| 5,520,692 A | 5/1996 | Ferrante |
| 5,522,843 A | 6/1996 | Zang |
| 5,522,844 A | 6/1996 | Johnson |
| 5,522,845 A | 6/1996 | Wenstrom, Jr. |
| 5,527,342 A | 6/1996 | Pietrzak et al. |
| 5,531,748 A | 7/1996 | de la Caffiniere |
| 5,534,001 A | 7/1996 | Schlapfer et al. |
| 5,534,011 A | 7/1996 | Greene, Jr. et al. |
| 5,534,031 A | 7/1996 | Matsuzaki et al. |
| 5,540,718 A | 7/1996 | Bartlett |
| 5,545,180 A | 8/1996 | Le et al. |
| 5,549,617 A | 8/1996 | Green et al. |
| 5,549,677 A | 8/1996 | Durr et al. |
| 5,556,428 A | 9/1996 | Shah |
| 5,562,664 A | 10/1996 | Durlacher et al. |
| 5,562,672 A | 10/1996 | Huebner et al. |
| 5,562,689 A | 10/1996 | Green et al. |
| 5,569,305 A | 10/1996 | Bonutti |
| 5,569,306 A | 10/1996 | Thal |
| 5,571,139 A | 11/1996 | Jenkins, Jr. |
| 5,573,547 A | 11/1996 | LeVeen et al. |
| 5,573,548 A | 11/1996 | Nazre et al. |
| 5,575,801 A | 11/1996 | Habermeyer et al. |
| 5,575,819 A | 11/1996 | Amis |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,839 A | 12/1996 | Gieringer |
| 5,584,860 A | 12/1996 | Goble et al. |
| 5,591,207 A | 1/1997 | Coleman |
| 5,593,410 A | 1/1997 | Vrespa |
| 5,593,425 A | 1/1997 | Bonutti et al. |
| 5,601,557 A | 2/1997 | Hayhurst |
| 5,601,558 A | 2/1997 | Torrie et al. |
| 5,607,432 A | 3/1997 | Fucci |
| 5,618,314 A | 4/1997 | Harwin et al. |
| 5,624,446 A | 4/1997 | Harryman, II |
| 5,626,612 A | 5/1997 | Bartlett |
| 5,626,613 A | 5/1997 | Schmieding |
| 5,628,766 A | 5/1997 | Johnson |
| 5,630,814 A | 5/1997 | Ross, Jr. et al. |
| 5,630,815 A | 5/1997 | Pohl et al. |
| 5,634,926 A | 6/1997 | Jobe |
| 5,637,112 A | 6/1997 | Moore et al. |
| 5,642,996 A | 7/1997 | Mochida et al. |
| 5,643,269 A | 7/1997 | Harle |
| 5,643,273 A | 7/1997 | Clark |
| 5,643,320 A | 7/1997 | Lower et al. |
| 5,643,321 A | 7/1997 | McDevitt |
| 5,645,545 A | 7/1997 | Bryant |
| 5,645,547 A | 7/1997 | Coleman |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,667,509 A | 9/1997 | Westin |
| D385,352 S | 10/1997 | Bales et al. |
| 5,676,665 A | 10/1997 | Bryan |
| 5,681,318 A | 10/1997 | Pennig et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,685,313 A | 11/1997 | Mayevsky |
| 5,690,649 A | 11/1997 | Li |
| 5,690,676 A | 11/1997 | DiPoto et al. |
| 5,690,677 A | 11/1997 | Schmieding et al. |
| 5,694,783 A | 12/1997 | Bartlett |
| 5,697,950 A | 12/1997 | Fucci et al. |
| 5,702,397 A | 12/1997 | Goble et al. |
| 5,702,398 A | 12/1997 | Tarabishy |
| 5,702,422 A | 12/1997 | Stone |
| 5,703,687 A | 12/1997 | Kumagai et al. |
| 5,707,373 A | 1/1998 | Sevrain et al. |
| 5,707,394 A | 1/1998 | Miller et al. |
| 5,709,708 A | 1/1998 | Thal |
| 5,713,900 A | 2/1998 | Benzel et al. |
| 5,720,765 A | 2/1998 | Thal |
| 5,720,766 A | 2/1998 | Zang et al. |
| 5,725,529 A | 3/1998 | Nicholson et al. |
| 5,725,541 A | 3/1998 | Anspach, III et al. |
| 5,728,136 A | 3/1998 | Thal |
| 5,733,307 A | 3/1998 | Dinsdale |
| 5,738,685 A | 4/1998 | Halm et al. |
| 5,741,259 A | 4/1998 | Chan |
| 5,741,300 A | 4/1998 | Li |
| 5,743,914 A | 4/1998 | Skiba |
| 5,747,712 A | 5/1998 | Goto |

(56) References Cited

U.S. PATENT DOCUMENTS

| | | |
|---|---|---|
| 5,749,878 A | 5/1998 | Bracy et al. |
| 5,755,542 A | 5/1998 | Janusz et al. |
| 5,755,721 A | 5/1998 | Hearn |
| 5,766,221 A | 6/1998 | Benderev et al. |
| 5,778,623 A | 7/1998 | Powell |
| 5,782,864 A | 7/1998 | Lizardi |
| 5,782,865 A | 7/1998 | Grotz |
| 5,782,866 A | 7/1998 | Wenstrom, Jr. |
| 5,792,142 A | 8/1998 | Galitzer |
| 5,797,914 A | 8/1998 | Leibinger |
| 5,797,963 A | 8/1998 | McDevitt |
| 5,800,433 A | 9/1998 | Benzel et al. |
| 5,800,447 A | 9/1998 | Wenstrom, Jr. |
| 5,807,396 A | 9/1998 | Raveh |
| 5,808,217 A | 9/1998 | Liao |
| 5,810,824 A | 9/1998 | Chan |
| 5,810,854 A | 9/1998 | Beach |
| 5,814,051 A | 9/1998 | Wenstrom, Jr. |
| 5,814,070 A | 9/1998 | Borzone et al. |
| 5,814,071 A | 9/1998 | McDevitt et al. |
| 5,816,812 A | 10/1998 | Kownacki et al. |
| 5,824,011 A | 10/1998 | Stone et al. |
| 5,827,291 A | 10/1998 | Fucci et al. |
| 5,843,082 A | 12/1998 | Yuan et al. |
| 5,843,087 A | 12/1998 | Jensen et al. |
| 5,843,127 A | 12/1998 | Li |
| 5,851,219 A | 12/1998 | Goble et al. |
| 5,860,978 A | 1/1999 | McDevitt et al. |
| 5,860,983 A | 1/1999 | Wenstrom, Jr. |
| 5,865,559 A | 2/1999 | Yang |
| 5,868,749 A | 2/1999 | Reed |
| 5,868,762 A | 2/1999 | Cragg et al. |
| 5,868,789 A | 2/1999 | Huebner |
| 5,879,372 A | 3/1999 | Bartlett |
| 5,885,294 A | 3/1999 | Pedlick et al. |
| 5,891,146 A | 4/1999 | Simon et al. |
| 5,891,168 A | 4/1999 | Thal |
| 5,893,850 A | 4/1999 | Cachia |
| 5,899,920 A | 5/1999 | DeSatnick et al. |
| 5,902,321 A | 5/1999 | Caspari et al. |
| 5,904,704 A | 5/1999 | Goble et al. |
| 5,911,721 A | 6/1999 | Nicholson et al. |
| 5,925,048 A | 7/1999 | Ahmad et al. |
| 5,931,844 A | 8/1999 | Thompson et al. |
| 5,935,129 A | 8/1999 | McDevitt et al. |
| 5,944,739 A | 8/1999 | Zlock et al. |
| 5,948,000 A | 9/1999 | Larsen et al. |
| 5,948,001 A | 9/1999 | Larsen |
| 5,951,559 A | 9/1999 | Burkhart |
| 5,957,953 A | 9/1999 | DiPoto et al. |
| 5,961,538 A | 10/1999 | Pedlick et al. |
| 5,964,764 A | 10/1999 | West, Jr. et al. |
| 5,964,783 A | 10/1999 | Grafton et al. |
| 5,968,044 A | 10/1999 | Nicholson et al. |
| 5,968,078 A | 10/1999 | Grotz |
| 5,980,558 A | 11/1999 | Wiley |
| 5,989,028 A | 11/1999 | Niznick |
| 5,993,451 A | 11/1999 | Burkhart |
| 5,993,459 A | 11/1999 | Larsen et al. |
| 5,997,541 A | 12/1999 | Schenk |
| 6,007,567 A | 12/1999 | Bonutti |
| 6,013,077 A | 1/2000 | Harwin |
| 6,013,083 A | 1/2000 | Bennett |
| 6,015,252 A | 1/2000 | Peck |
| 6,019,768 A | 2/2000 | Wenstrom, Jr. et al. |
| 6,022,373 A | 2/2000 | Li |
| 6,024,758 A | 2/2000 | Thal |
| 6,027,523 A | 2/2000 | Schmieding |
| 6,030,162 A | 2/2000 | Huebner |
| 6,036,694 A | 3/2000 | Goble et al. |
| 6,042,583 A | 3/2000 | Thompson et al. |
| 6,045,554 A | 4/2000 | Grooms et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,077,267 A | 6/2000 | Huene |
| 6,086,365 A | 7/2000 | Fields |
| 6,086,608 A | 7/2000 | Ek et al. |
| 6,090,110 A | 7/2000 | Metz-Stavenhagen |
| 6,096,041 A | 8/2000 | Gellman et al. |
| 6,099,547 A | 8/2000 | Gellman et al. |
| 6,117,161 A | 9/2000 | Li et al. |
| 6,117,162 A | 9/2000 | Schmieding et al. |
| 6,129,762 A | 10/2000 | Li |
| 6,143,017 A | 11/2000 | Thal |
| 6,149,669 A | 11/2000 | Li |
| 6,156,039 A | 12/2000 | Thal |
| 6,159,235 A | 12/2000 | Kim |
| 6,162,234 A | 12/2000 | Freedland et al. |
| 6,183,479 B1 | 2/2001 | Tormala et al. |
| 6,200,329 B1 | 3/2001 | Fung et al. |
| 6,214,031 B1 | 4/2001 | Schmieding |
| 6,221,107 B1 | 4/2001 | Steiner et al. |
| 6,231,592 B1 | 5/2001 | Bonutti et al. |
| 6,231,606 B1 | 5/2001 | Graf et al. |
| 6,280,474 B1 | 8/2001 | Cassidy et al. |
| 6,287,324 B1 | 9/2001 | Yarnitsky et al. |
| 6,319,270 B1 | 11/2001 | Grafton et al. |
| 6,319,271 B1 | 11/2001 | Schwartz et al. |
| 6,355,053 B1 | 3/2002 | Li |
| 6,368,322 B1 | 4/2002 | Luks et al. |
| 6,387,129 B2 | 5/2002 | Rieser et al. |
| 6,436,124 B1 | 8/2002 | Anderson et al. |
| 6,436,142 B1 | 8/2002 | Paes et al. |
| RE37,963 E | 1/2003 | Thal |
| 6,508,830 B2 | 1/2003 | Steiner |
| 6,511,499 B2 | 1/2003 | Schmieding et al. |
| 6,517,542 B1 | 2/2003 | Papay et al. |
| 6,517,564 B1 | 2/2003 | Grafton et al. |
| 6,520,980 B1 | 2/2003 | Foerster |
| 6,524,317 B1 | 2/2003 | Ritchart et al. |
| 6,527,772 B2 | 3/2003 | Enayati |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,551,330 B1 | 4/2003 | Bain et al. |
| 6,558,389 B2 | 5/2003 | Clark et al. |
| 6,562,044 B1 | 5/2003 | Cooper |
| 6,585,730 B1 | 7/2003 | Foerster |
| 6,610,080 B2 | 8/2003 | Morgan |
| 6,616,665 B2 | 9/2003 | Grafton et al. |
| 6,629,977 B1 | 10/2003 | Wolf |
| 6,635,074 B2 | 10/2003 | Bartlett |
| 6,641,596 B1 | 11/2003 | Lizardi |
| 6,641,597 B2 | 11/2003 | Burkhart et al. |
| 6,648,903 B1 | 11/2003 | Pierson, III |
| 6,652,561 B1 | 11/2003 | Tran |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,666,877 B2 | 12/2003 | Morgan et al. |
| 6,685,728 B2 | 2/2004 | Sinnott et al. |
| 6,692,516 B2 | 2/2004 | West, Jr. et al. |
| 6,699,250 B1 | 3/2004 | Osterle et al. |
| 6,716,234 B2 | 4/2004 | Grafton et al. |
| 6,770,076 B2 | 8/2004 | Foerster |
| 6,770,084 B1 | 8/2004 | Bain et al. |
| 6,773,450 B2 | 8/2004 | Leung et al. |
| 6,780,198 B1 | 8/2004 | Gregoire et al. |
| 6,818,010 B2 | 11/2004 | Eichhorn et al. |
| 6,840,953 B2 | 1/2005 | Martinek |
| 6,857,520 B2 | 2/2005 | Salazar et al. |
| 6,875,216 B2 | 4/2005 | Wolf |
| 6,916,333 B2 | 7/2005 | Schmieding et al. |
| 6,923,824 B2 | 8/2005 | Morgan et al. |
| 6,932,834 B2 | 8/2005 | Lizardi et al. |
| 6,981,974 B2 | 1/2006 | Berger |
| 7,037,324 B2 | 5/2006 | Martinek |
| 7,083,638 B2 | 8/2006 | Foerster |
| 7,083,683 B2 | 8/2006 | Schneidereit et al. |
| 7,090,690 B2 | 8/2006 | Foerster et al. |
| 7,195,634 B2 | 3/2007 | Schmieding et al. |
| 7,204,839 B2 | 4/2007 | Dreyfuss et al. |
| 7,211,088 B2 | 5/2007 | Grafton et al. |

(56) References Cited

U.S. PATENT DOCUMENTS

| | | |
|---|---|---|
| 7,217,279 B2 | 5/2007 | Reese |
| 7,247,164 B1 | 7/2007 | Ritchart et al. |
| 7,322,978 B2 | 1/2008 | West, Jr. |
| 7,322,986 B2 | 1/2008 | Wolf |
| 7,329,272 B2 | 2/2008 | Burkhart et al. |
| 7,491,217 B1 | 2/2009 | Hendren et al. |
| 7,517,357 B2 | 4/2009 | Abrams et al. |
| 7,556,640 B2 | 7/2009 | Foerster |
| 7,637,949 B2 | 12/2009 | Hart |
| 7,651,495 B2 | 1/2010 | McDevitt et al. |
| 7,695,495 B2 | 4/2010 | Dreyfuss |
| 7,785,347 B2 | 8/2010 | Harvie et al. |
| 7,803,173 B2 | 9/2010 | Burkhart et al. |
| 7,883,528 B2 | 2/2011 | Grafton et al. |
| 7,883,529 B2 | 2/2011 | Sinnott et al. |
| 7,887,551 B2 | 2/2011 | Bojarski et al. |
| 7,965,494 B1 | 6/2011 | Morris et al. |
| 7,981,140 B2 | 7/2011 | Burkhart |
| 7,993,369 B2 | 8/2011 | Dreyfuss |
| 8,105,343 B2 | 1/2012 | White et al. |
| 8,133,258 B2 | 3/2012 | Foerster et al. |
| 8,137,381 B2 | 3/2012 | Foerster et al. |
| 8,317,829 B2 | 11/2012 | Foerster et al. |
| 8,343,186 B2 | 1/2013 | Dreyfuss et al. |
| 8,444,672 B2 | 5/2013 | Foerster |
| 8,623,052 B2 | 1/2014 | Dreyfuss et al. |
| 8,764,797 B2 | 7/2014 | Dreyfuss et al. |
| 8,801,755 B2 | 8/2014 | Dreyfuss et al. |
| 8,821,541 B2 | 9/2014 | Dreyfuss et al. |
| 9,179,907 B2 | 11/2015 | Elattrache et al. |
| 2001/0002439 A1 | 5/2001 | Bonutti et al. |
| 2001/0014814 A1 | 8/2001 | Bonutti et al. |
| 2001/0018613 A1 | 8/2001 | Huene |
| 2001/0021862 A1 | 9/2001 | Bonutti et al. |
| 2002/0013608 A1 | 1/2002 | ElAttrache et al. |
| 2002/0052629 A1 | 5/2002 | Morgan et al. |
| 2002/0087190 A1 | 7/2002 | Benavitz et al. |
| 2002/0111653 A1 | 8/2002 | Foerster |
| 2002/0128684 A1 | 9/2002 | Foerster |
| 2002/0147463 A1 | 10/2002 | Martinek |
| 2002/0188305 A1 | 12/2002 | Foerster et al. |
| 2003/0004545 A1 | 1/2003 | Burkhart et al. |
| 2003/0065361 A1* | 4/2003 | Dreyfuss ............ A61B 17/0401 606/232 |
| 2003/0069604 A1 | 4/2003 | Schmieding et al. |
| 2003/0144696 A1 | 7/2003 | Sinnott et al. |
| 2003/0149448 A1 | 8/2003 | Foerster et al. |
| 2003/0187444 A1 | 10/2003 | Overaker et al. |
| 2003/0191498 A1 | 10/2003 | Foerster et al. |
| 2003/0195563 A1 | 10/2003 | Foerster |
| 2003/0204193 A1 | 10/2003 | Gabriel et al. |
| 2004/0030354 A1 | 2/2004 | Leung et al. |
| 2004/0093031 A1 | 5/2004 | Burkhart et al. |
| 2004/0106950 A1 | 6/2004 | Grafton et al. |
| 2004/0133239 A1 | 7/2004 | Singhatat |
| 2004/0138683 A1 | 7/2004 | Shelton et al. |
| 2004/0138706 A1 | 7/2004 | Abrams et al. |
| 2004/0267316 A1 | 12/2004 | Powell et al. |
| 2005/0222618 A1 | 10/2005 | Dreyfuss et al. |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2005/0283158 A1 | 12/2005 | West, Jr. |
| 2006/0004364 A1 | 1/2006 | Green et al. |
| 2006/0074434 A1 | 4/2006 | Wenstrom, Jr. et al. |
| 2006/0079904 A1 | 4/2006 | Thal |
| 2006/0100630 A1 | 5/2006 | West, Jr. |
| 2006/0271060 A1 | 11/2006 | Gordon |
| 2007/0142838 A1 | 6/2007 | Jordan |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0191849 A1 | 8/2007 | ElAttrache et al. |
| 2007/0225719 A1 | 9/2007 | Stone et al. |
| 2007/0255317 A1 | 11/2007 | Fanton et al. |
| 2007/0260259 A1 | 11/2007 | Fanton et al. |
| 2008/0004659 A1 | 1/2008 | Burkhart et al. |
| 2009/0187216 A1 | 7/2009 | Schmieding et al. |
| 2011/0015674 A1 | 1/2011 | Howard et al. |

FOREIGN PATENT DOCUMENTS

| | | |
|---|---|---|
| EP | 0574707 A1 | 12/1993 |
| EP | 0598219 A2 | 5/1994 |
| EP | 0465910 B1 | 11/1995 |
| EP | 0686373 A1 | 12/1995 |
| EP | 0687446 A2 | 12/1995 |
| EP | 0699420 A2 | 3/1996 |
| EP | 0835640 A1 | 4/1998 |
| EP | 0951869 A1 | 10/1999 |
| EP | 1016377 | 7/2000 |
| EP | 1530951 A2 | 5/2005 |
| EP | 1762186 A3 | 3/2007 |
| EP | 1797826 B1 | 12/2009 |
| FR | 2588332 | 4/1987 |
| FR | 2622430 | 10/1987 |
| FR | 2717070 A1 | 9/1995 |
| FR | 2725615 A1 | 4/1996 |
| FR | 2738737 A1 | 3/1997 |
| GB | 651009 | 3/1951 |
| GM | 7717562 | 10/1977 |
| SU | 1034734 | 8/1983 |
| SU | 1600713 A1 | 10/1990 |
| WO | 94/28811 A1 | 12/1994 |
| WO | 95/22930 A1 | 8/1995 |
| WO | 96/14798 A1 | 5/1996 |
| WO | 96/41574 A2 | 12/1996 |
| WO | 98/26717 A1 | 6/1998 |
| WO | 99/37217 | 7/1999 |
| WO | 99/53844 A1 | 10/1999 |
| WO | 01/10312 A1 | 2/2001 |
| WO | 02/21998 A2 | 3/2002 |
| WO | 2009/055075 | 4/2009 |

OTHER PUBLICATIONS

George, MD, Michael S. et al., Suture Anchors in Arthroscopic Rotator Cuff Repair, Operative Techniques in Sports Medicine, 2004, pp. 210-214.

Millett, MD, Peter J., Mattress Double Anchor Footprint Repair: A Novel, Arthroscopic Rotator Cuff Repair Technique, Arthroscopy: The Journal of Arthroscopic and Related Surgery, vol. 20, No. 8 Oct. 2004: pp. 875-879.

Robbe, MD, Rudy et al., Knotless Suture-Based Anchors, Operative Techniques in Sports Medicine, 2004, pp. 221-224.

Thal, MD, Raymond, Knotless Suture Anchor, Arthroscopic Bankart Repair Without Tying Knots, Clinical Orthopaedics and Related Research, No. 390, 2001, pp. 42-51.

Waltrip, Robert L., Rotator Cuff Repair: A Biomechanical Comparison of Three Techniques, The American Journal of Sports Medicine, vol. 31, No. 4, 2003., pp. 493-497.

Yian, M.D., Edward et al., Arthroscopic Repair of SLAP Lesions With a Bioknotless Suture Anchor, Arthroscopy: The Journal of Arthroscopic and Related Surgery, vol. 20, No. 5, May-Jun. 2004: pp. 547-551.

Zumstein, M.D., Matthias, In Vitro Comparison of Standard and Knotless Metal Suture Anchors, Arthroscopy: The Journal of Arthroscopic and Related Surgery, vol. 20, No. 5 May-Jun. 2004: pp. 517-520.

"The AutoCuff™ System," Opus Medical, 2003.

510(k) Summary of Safety and Effectiveness, DePuy Inc, Feb. 6, 1997.

Abrams, Jeffrey S., et al., Arthroscopic Rotator Cuff Surgery, A Practical Approach to Management, 2008.

Arthrex is Reaching New Heights in Rotator Cuff Repair, Arthrex, Inc., 2007.

Barber, M.D., F. Alan, Biodegradable Shoulder Anchors Have Unique Modes of Failure, Arthroscopy: The Journal of Arthroscopic and Related Surgery, vol. 23, No. 3 Mar. 2007, pp. 316-320.

(56) References Cited

OTHER PUBLICATIONS

Barber, M.D., F. Alan et al., Biomechanical Analysis of Pullout Strength of Rotator Cuff and Glenoid Anchors: 2011 Update, Arthroscopy: The Journal of Arthroscopic and Related Surgery, vol. 27, No. 7 Jul. 2011; pp. 895-905.

Barber, M.D., F. Alan et al., The In Vivo Histology of an Absorbable Suture Anchor: A Preliminary Report, Arthroscopy: The Journal of Arthroscopic and Related Surgery, vol. 11, No. 1 Feb. 1995, pp. 77-81.

Barber, M.D., F. Alan et al., Suture Anchor Failure Strength—An In Vivo Study, Arthroscopy: The Journal of Arthroscopic and Related Surgery, vol. 9, No. 6, 1993., pp. 647-652.

Barber, M.D., F. Alan et al., Suture Anchor Strength Revisited, Arthroscopy: The Journal of Arthroscopic and Related Surgery, vol. 12, No. 1 Feb. 1996: pp. 32-38.

Barber, M.D., F. Alan et al., Suture Anchors—Update 1999, Arthroscopy: The Journal of Arthroscopic and Related Surgery, vol. 15, No. 7, Oct. 1999: pp. 719-725.

Barber, M.D., F. Alan et al., The Ultimate Strength of Suture Anchors, Arthroscopy: The Journal of Arthroscopic and Related Surgery, vol. 11, No. 1 Feb. 1995: pp. 21-28.

Barber, M.D., F. Alan et al., Sutures and Suture Anchors: Update 2003, Arthroscopy: The Journal of Arthroscopic and Related Surgery, vol. 19, No. 9 Nov. 2003: pp. 985-990.

Barber, M.D., F. Alan et al., Sutures and Suture Anchors: Update 2006, Arthroscopy: The Journal of Arthroscopic and Related Surgery, vol. 22, No. 10 Oct. 2006: pp. 1063-1069.

Barber, M.D., F. Alan et al., Suture Anchor Materials, Eyelets, and Designs: Update 2008, Arthroscopy: The Journal of Arthroscopic and Related Surgery, vol. 24, No. 8 Aug. 2008: pp. 859-867.

Bioknotless™ Anchor, The First Absorbable Knotless Suture Anchor, Mitek® Products, 2001.

Burkhart, Stephen S. et al., Chapter 4, Current Concepts of Rotator Cuff Repair, pp. 81-88.

Burkhart M.D., Stephen S. et al., Cyclic Loading of Anchor-Based Rotator Cuff Repairs: Confirmation of the Tension Overload Phenomenon and Comparison of Suture Anchor Fixation With Transosseous Fixation, Arthroscopy: The Journal of Arthroscopic and Related Surgery, vol. 13, No. 6 Dec. 1997: pp. 720-724.

Burkhart, M.D., Stephen S., The Deadman Theory of Suture Anchors: Observations Along a South Texas Fence Line, Arthroscopy: The Journal of Arthroscopic and Related Surgery, vol. 11, No. 1 Feb. 1995: pp. 119-123.

Burkhart M.D., Stephen S., Partial Repair of Irreparable Rotator Cuff Tears, Arthroscopy: The Journal of Arthroscopic and Related Surgery, vol. 10, No. 4, 1994, pp. 363-370.

Burkhart M.D., Stephen S., SLAP Lesions in Association with Complete Tears of the Long Head of the Biceps Tendon: A Report of Two Cases, Arthroscopy: The Journal of Arthroscopic and Related Surgery, vol. 8, No. 1, 1992, pp. 31-35.

Craft M.D., David V et al., Fixation strength of rotator cuff repairs with suture anchors and the transosseous suture technique, Journal of Shoulder and Elbow Surgery Board of Trustees, 1996, pp. 32-40.

Denard, M.D., Patrick J., The Evolution of Suture Anchors in Arthroscopic Rotator Cuff Repair, Arthroscopy: The Journal of Arthroscopic and Related Surgery, vol. 29, No. 9 Sep. 2013: pp. 1589-1595.

Gerber, Christian et al., Mechanical Strength of Repairs of the Rotator Cuff, The Journal of Bone and Joint Surgery, vol. 76-B, No. 3, May 1994, pp. 371-380.

Harryman, II, M.D., Douglas T., Repairs of the Rotator Cuff, Correlation of Functional Results with Integrity of the Cuff, The Journal of Bone and Joint Surgery, vol. 73-A, No. 7, Aug. 1991, pp. 982-989.

Hecker, Aaron T. et al., Pull-out strength of suture anchors for rotator cuff and Bankart lesion repairs, The American Journal of Sports Medicine, vol. 21, No. 6, 1993, pp. 874-879.

Johnson, MD, FRCS, Donald H. et al., Chapter 20: Thermal Treatment, Sutures, Knots, and Bone Anchors, Practical Orthopaedic Sports Medicine and Arthroscopy, 2007, pp. 303-305.

Lovald Ph.D, Scott et al., Chapter 15: Applications and Polyetheretherketone in Trauma, Arthroscopy, and Cranial Defect Repair, PEEK Biomaterials Handbook, 2012, pp. 243-260.

Ma, Richard et al., Arthroscopic rotator cuff repair: suture anchor properties, modes of failure and technical considerations, Expert Rev. Med. Devices 8(3), 2011, pp. 377-387.

Meyer, M.D., Dominik C., Failure of Suture Material at Suture Anchor Eyelets, Arthroscopy: The Journal of Arthroscopic and Related Surgery, vol. 18, No. 9 Nov.-Dec. 2002: pp. 1013-1019.

Millstein, M.D., Eric S. et al., Instructional Course 302: Arthroscopic Management of Partial, Full-Thickness, and Complex Rotator Cuff Tears: Indications, Techniques, and Complications, Arthroscopy: The Journal of Arthroscopic and Related Surgery, vol. 19, No. 10 (December, Suppl 1), 2003: pp. 189-199.

Ono, Ichiro et al., Evaluation of a high density polyethylene fixing system for hydroxyapatite ceramic implants, Biomaterials 21 (2000), pp. 143-151.

Pietschmann, M.D., Matthias F., Biomechanical Stability of Knotless Suture Anchors Used in Rotator Cuff Repair in Healthy and Osteopenic Bone, Arthroscopy: The Journal of Arthroscopic and Related Surgery, vol. 26, No. 8 Aug. 2010: pp. 1035-1044.

Reed, Stephen C., Full Thickness Rotator Cuff Tears, A Biomechanical Comparison of Suture Versus Bone Anchor Techniques, The American Journal of Sports Medicine, vol. 24, No. 1, 1996: pp. 46-48.

Richmond, John C., Modification of the Bankart reconstruction with a suture anchor, Report of a new technique, The American Journal of Sports Medicine, vol. 19, No. 4, 1991: pp. 343-346.

Rupp, M.D., Stefan, Fatigue Testing of Suture Anchors, The American Journal of Sports Medicine, vol. 30, No. 2, 2002, pp. 239-247.

Snyder, M.D., Stephen J., Technique of Arthroscopic Rotator Cuff Repair Using Implantable 4-MM REVO Suture Anchors, Suture Shuttle Relays, and No. 2 Nonabsorbable Mattress Sutures, The Rotator Cuff, Part II, Orthopedic Clinics of North America, vol. 28, No. 2, Apr. 1997, pp. 267-275.

Weideman, Ph.D., Carol A., 510(k) Summary of Safety and Effectiveness, Mar. 21, 1997.

Wolf, M.D., Eugene M., Arthroscopic Bankart Repair Using Suture Anchors, Operative Techniques in Orthopaedics, vol. 1, No. 2 Apr. 1991: pp. 184-191.

Wolf, M.D., Eugene M., Arthroscopic Capsulolabral Repair Using Suture Anchors, Shoulder Arthroscopy and Related Surgery, Orthopedic Clinics of North America, vol. 24, No. 1, Jan. 1993, pp. 59-69.

510(K) Summary for Arthrex, Inc.'s Bio-Interference Screw, Jul. 9, 1997.

Ahmad MD, Christopher S., Arthroscopic biceps tenodesis, Orthopedi Clinics of North America, 2003, pp. 499-506.

An Absorbable Interference Screw . . . The difference is Acufex, Acufex, Smith & Nephew Endoscopy, 1995.

Arthrex Corkscrew™ Suture Anchors, 1996.

Arthrex Surgical Techniques, https://web.archive.org/web/19981206111626/http://www.arthrex.com/Procedures.htm; Dec. 6, 1998.

Welcome to Arthrex, https://web.archive.org/web/19981111190428/http://www.arthrex.com/; Nov. 11, 1998.

Bach, Jr. M.D., Bernard R., Observations on Interference Screw Morphologies, Arthroscopy: The Journal of Arthroscopic and Related Surgery, vol. 16, No. 5 Jul.-Aug. 2000: E10, pp. 1-6.

Barber, M.D., F. Alan et al., Preliminary Results of an Absorbably Interference Screw, Arthroscopy: The Journal of Arthroscopic and Related Surgery, vol. 11, No. 5 Oct. 1995: pp. 537-548.

Bellemans, M.D.,Ph.D, Johan, A Modified Technique for Tibial Interference Screw Fixation of Hamstring Anterior Cruciate Ligament Grafts, Arthroscopy: The Journal of Arthroscopic and Related Surgery, vol. 15, No. 6 Sep. 1999: pp. 669-671.

Benterud, Jan G. et al., Implant holding power of the femoral head, Acta Orthop Scand 119; 63(1): pp. 47-49.

Caborn, M.D., David N. M. et al., Quadruped Semitendinosus-Gracilis Autograft Fixation in the Femoral Tunnel: A Comparison Between a Metal and a Bioabsorbably Interference Screw, Arthroscopy: The Journal of Arthroscopic and Related Surgery, vol. 14, No. 3 Apr. 1998: pp. 241-245.

(56) References Cited

OTHER PUBLICATIONS

Chapman, J.R. et al., Factors Affecting the Pullout Strength of Cancellous Bone Screws, Journal of Biomechanical Enginnering, Aug. 1996, vol. 11, pp. 391-398.
Corry, MD, FRCS(Orth), Ian S. et al., Arthroscopic Reconstruction of the Anterior Cruciate Ligament, The American Journal of Sports Medicine, vol. 27, No. 3, 1999, pp. 444-454.
The products you Need . . . The convenience you want . . . and the value you deserve., Acufex Microsurgical, Inc., 1994.
Lambert, M.D., Kenneth L., Vascularized Patellar Tendon Graft with Rigid Internal Fixation for Anterior Cruciate Ligament Insufficiency, Clinical Orthopaedics and Related Research, Jan.-Feb. 1983, pp. 85-89.
Lo, MD, Ian K.Y. et al., Arthroscopic Biceps Tenodesis: Indications and Technique, Operative Techniques in Sports Medicine, vol. 10, No. 2 Apr. 2002: pp. 105-112.
Mazzocca, MD, A.D. et al., Single Incision Technique Using an Interference Screw for the Repair of Distal Biceps Tendon Ruptures, Operative Techniques in Sports Medicine, vol. 11, No. 1 Jan. 2003: pp. 36-41.
Pearls of Wisdom, https://web.archive.org/web/19981201194509/http://www.arthrex.com/pearls.htm, Dec. 1, 1998.
Perren, SM et al., Technical and biomechanical aspects of screws used for bone surgery, International Journal of Orthopaedic Trauma 1992; 2: pp. 31-48.
Rehnberg, Lars et al., Uppsala Screw Fixation Versus the von Bahr Technique in Displaced Cervical Hip Fractures: Preliminary Report, Journal of Orthopaedic Trauma, vol. 3, No. 1, 1989, pp. 48-52.
Richards, MD, David P. et al., Arthroscopic Biceps Tenodesis with Interference Screw Fixation: The Lateral Decubitus Position, Operative Techniques in Sports Medicine, vol. 11, No. 1 Jan. 2003; pp. 15-23.
Rupp, MD, Stefan et al., Fixation Strength of a Biodegradable Interference Screw and a Press-Fit Technique in Anterior Cruciate Ligament Reconstruction With a BPTB Graft, Arthroscopy: The Journal of Arthroscopic and Related Surgery, vol. 13, No. 1 Feb. 1997: pp. 61-65.
Caborn, M.D., David et al., Arthroscopic Repair of a Bankart Lesion Using TAG® Suture Anchors, Smith & Nephew Endoscopy, 1996.
Smith & Nephew, 1997 Products Catalog.
Tencer, Allen F. et al., Biomechanics of Cannulated and Noncannulated Screws, Cannulated Screw Fixation, 1996, pp. 15-40.
McGuire, MD, David A., The BioScrew® Fixation System, Linvatec, 1995.
Uhl, MD, Richard L., The Biomechanice of Screws, Orthopaedic Review, vol. XVIII, No. 12, Dec. 1989, pp. 1302-1307.
Using the T-Fix, Acufex Microsurgical, Inc., 1995.
Von Bahr, Viktor et al., Osteosynthesis of Femoral Neck Fracture Using Screws, Acta Chir Scand 140; pp. 277-282, 1974.
Weiler, MD, Andreas et al., Biodegradable Interference Screw Fixation Exhibits Pull-Out Force and Stiffness Similar to Titanium Screws, The American Journal of Sports Medicine, vol. 26, No. 1, 1998, pp. 119-128.
Weiler, MD, Andreas et al, Hamstring Tendon Fixation Using Interference Screws: A Biomechanical Study in Calf Tibial Bone, Arthroscopy: The Journal of Arthroscopic and Related Surgery, vol. 14, No. 1 Jan.-Feb. 1998: pp. 29-37.
510(K) Summary for Arthrex, Inc.'s FASTak Suture Anchor, Apr. 18, 1996.
Stadelmaier, DO, Denise M. et al., "Cyclic Pull-Out Strength of Hamstring Tendon Graft Fixation with Soft Tissue Interference Screws" The American Journal of Sports Medicine, vol. 27, No. 6, 1999, pp. 778-783.
Kurosaka, MD, Masahiro et al., "A biomechanical comparison of different surgical techniques of graft fixation in anterior cruciate ligament reconstruction" The American Journal of Sports Medicine, vol. 15, No. 3, 1987, pp. 225-229.
U.S. Food and Drug Administration Guidance: Use of International Standard ISO-10993, 'Biological Evaluation of Medical Devices Part 1: Evaluation and Testing', 1995.
Hayes, "Biomechanics of Cortical and Trabecular Bone: Implications for Assessment of Fracture Risk," Basic Orthopaedic Biomechanics, pp. 93-142 (1991).
Petition for Inter Partes Review of U.S. Pat. No. 8,343,186, filed in the United States Patent and Trademark Office on Jan. 27, 2016, Case No. IPR2016-00505.
Petition for Inter Partes Review of U.S. Pat. No. 8,623,052, filed in the United States Patent and Trademark Office on Jan. 27, 2016, Case No. IPR2016-00506.
Petition for Inter Partes Review of U.S. Pat. No. 8,801,755, filed in the United States Patent and Trademark Office on Jan. 27, 2016, Case No. IPR2016-00507.
Petition for Inter Partes Review of U.S. Pat. No. 8,801,755, filed in the United States Patent and Trademark Office on Jan. 27, 2016, Case No. IPR2016-00508.
Defendants' Invalidity Contentions and Production of Documents Pursuant to Patent Rules 3-3 and 3-4(B), *Arthrex, Inc.* v. *Smith & Nephew, Inc. and Arthrocare Corp.*, Civil Action No. 2:15-CV-1047-RSP; filed Nov. 18, 2015.
Corkscrew Product Sheet from Arthrex Catalog 1998-1999.
Oberg et al., "Screw Threads" Machinery's Handbook: A Reference Book for the Mechanical Engineer, Manufacturing Engineer, Draftsman, Toolmaker, and Machinist, pp. 1633, Industrial Press Inc., New York, NY (1996).
Goradia, M.D., Vipool K. et al., "Cyclic Loading of Rotator Cuff Repairs: A Comparison of Bioabsorbable Tacks With Metal Suture Anchors and Transosseous Sutures" Arthroscopy: The Journal of Arthroscopic and Related Surgery, vol. 17, No. 4 Apr. 2001: pp. 360-364.
Goble, M.D., E. Marlowe, "The Development of Suture Anchors for Use in Soft Tissue Fixation to Bone" The American Journal of Sports Medicine, vol. 22, No. 2, 1994.
Lajtai, G. et al., Shoulder Arthroscopy and MRI Techniques, 2003.
Asnis et al., "Cancellous Bone Screw Design and Holding Power," 62nd Annual Meeting of American Academy of Orthopaedic Surgeons, pp. 465-466 (Feb. 1995).
Decoster, Thomas A. et al., "Optimizing Bone Screw Pullout Force," Journal of Orthopaedic Trauma, vol. 4, No. 2, pp. 169-174, 1990.
Orthopedics, Feb. 1997, vol. 20, No. 2, pp. 160, 174 and 182.
Petition for Inter Partes Review of U.S. Pat. No. 8,821,541, filed in the United States Patent and Trademark Office on Apr. 19, 2016, Case No. IPR2016-00917.
Petition for Inter Partes Review of U.S. Pat. No. 8,821,541, filed in the United States Patent and Trademark Office on Apr. 19, 2016, Case No. IPR2016-00918.
Decision—Institution of Inter Partes Review of U.S. Pat. No. 8,343,186 dated Jul. 27, 2016, Case IPR2016-00505, from the United States Patent and Trademark Office.
Decision—Institution of Inter Partes Review of U.S. Pat. No. 8,623,052 dated Aug. 2, 2016, Case IPR2016-00506, from the United States Patent and Trademark Office.
Decision—Institution of Inter Partes Review of U.S. Pat. No. 8,801,755 dated Jul. 27, 2016, Case IPR2016-00507, from the United States Patent and Trademark Office.
Decision—Institution of Inter Partes Review of U.S. Pat. No. 8,801,755 dated Jul. 27, 2016, Case IPR2016-00508, from the United States Patent and Trademark Office.
European Search Report for EP Application No. 05102676.3 dated Aug. 29, 2005.
"Bone Screw Technical Information," Richards Manufacturing Company, Inc. Tech. Publ. 1980, pp. 1-14.
"Implants for Surgery-Metal Bone Screws With Hexagonal Drive Connection, Spherical Under-Surface of Head, Asymmetrical Thread-Dimensions," International Standard ISO 5834, 1991(E), pp. 1-10.
Linvatec Revo Cancellous Screw Advertisement, 1993.
R.M. Altieri Mitek Surgical Products announces fourth-quarter and year-end results, Business Wire (Feb. 24, 1995).
Rupp et al., "Fatigue Testing of Suture Anchors," The American Journal of Sports Medicine, Mar. 2002, vol. 30, No. 2, pp. 239-247.
Laws, "Suturing Techniques," Principles of Laparoscopic Surgery, 1995, pp. 35-45.

(56) References Cited

OTHER PUBLICATIONS

Bacilla M.D., Phillip, "Arthroscopic Bankart Repair in a High Demand Patient Population", Arthroscopy: The Journal of Arthroscopic and Related Surgery, vol. 13, No. 1, Feb. 1997, pp. 51-60.
All Soft Tissue Anchors Are Not Created Equal . . . , Orthopaedic Biosystems Ltd., Inc., 1996.
M3-X Extremity Fixation System Just Drill and Drive, Osteomed Corporation, 1994.
Mitek GII Anchor™ System, Instrument Guide/Ordering Information, Mitek® Surgical Products, Inc., 1994.
Mitek GII Anchor™ System, Instrument Guide/Ordering Information, 1994.
Bradley M.D., James P., Labral Repair With Statak, Linvatec, 1994.
Your open techniques work . . . Let Our Arthroscopic Tools Work for You, Innovasive® Devices, Inc., 1995.
Snyder, M.D., Stephen, The Mini-Revo Labral Repair System, Linvatec, 1994.
Higgins, MD et al., Laurence D., Arthroscopic Bankart Repair, Operative Technique and Surgical Pitfalls, Clinics in Sports Medicine, vol. 19, No. 1, Jan. 2000, pp. 49-62.
Cole, MD, MBA et al., Brian J., Arthroscopic Shoulder Stabilization With Suture Anchors: Technique, Technology, and Pitfalls, Clinical Orthopaedics and Related Research, vol. 390, Sep. 2001, pp. 17-30.
Barber, M.D., F. Alan et al., Internal Fixation Strength of Suture Anchors—Update 1997, Arthroscopy: The Journal of Arthroscopic and Related Surgery, vol. 13, No. 3 Jun. 1997, pp. 355-362.
Goble, E. Marlowe et al., The Development of Suture Anchors for Use in Soft Tissue Fixation to Bone, The American Journal of Sports Medicine, vol. 22, No. 2, 1994, pp. 236-239.
Chang, D.P.M., Thomas J., Soft Tissue Anchors: An Update, Chapter 50, pp. 301-305.
Labral Repair with Statak® Suture Anchors, Surgical Techniques, Arthroscopic & Open, Zimmer, 97-2344-03, 1996.
Statak™ Soft Tissue Attachment Device Technique Guide, Surgical Techniques, Common Foot Procedures, Zimmer, 97-2344-58 Rev. 1, 1995.
Rotator Cuff Repair with Statak® Suture Anchors Technique Guide, Surgical Techniques, Arthroscopic & Open, Zimmer, 97-2344-04, 1996.
Pederson, DPM, Bradley et al., Mitek® Anchor System: A New Technique for Tenodesis and Ligamentous Repair of the Foot and Ankle, The Journal of Foot Surgery, vol. 30, No. 1, 1991, pp. 48-51.
Yu, DPM, Gerard V. et al., Soft Tissue Anchors, 1992, pp. 120-125.
IMF Screw Set for Intermaxillary Fixation, SYNTHES® Maxillofacial, 2001.
Stryker Leibinger, IMF Screw System for Intermaxillary Fixation Brochure.
Arthur, DMD, Gregory et al., A Simplified Technique of Maxillomandibular Fixation, American Association of Oral and Maxillofacial Surgeons, 1989, p. 1234.
Busch, M.D., D.D.S, Richard F., Maxillomandibular Fixation Utilizing Cortical Bone Screws, Correspondence and Brief Communications, p. 262.
Karlis, D.M.D., Vasiliki et al., Reply, Plastic and Reconsdtructive Surgery, Apr. 1998, p. 1414.
Karlis, D.M.D, Vasiliki et al., An Alternative to Arch-Bar Maxillomandibular Fixation, Ideas and Innovations, vol. 99, No. 6, 1996, pp. 1758-1759.
Martin FAMI Screws Brochure.
Mondeal IMF Quick-Fix System Brochure.
Judgment—Granting Request for Adverse Judgment Before Institution of Trial 37 C.F.R. § 42.73(b) dated Sep. 21, 2016, Case IPR2016-00917, from the United States Patent and Trademark Office.
Decision—Granting Institution of Inter Partes Review 37 C.F.R. § 42.108 dated Oct. 17, 2016, Case IPR2016-00918, from the United States Patent and Trademark Office.

* cited by examiner

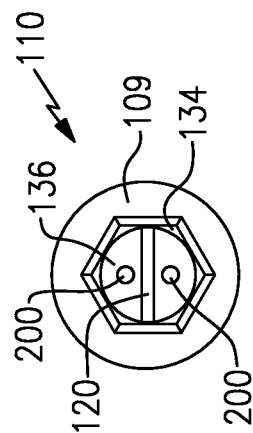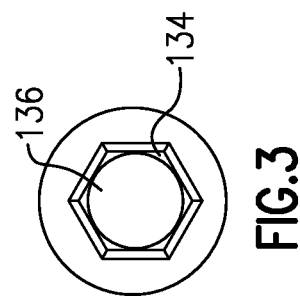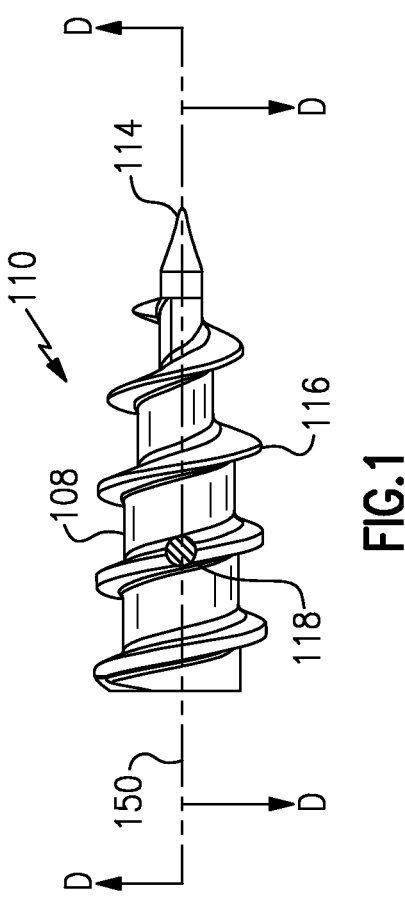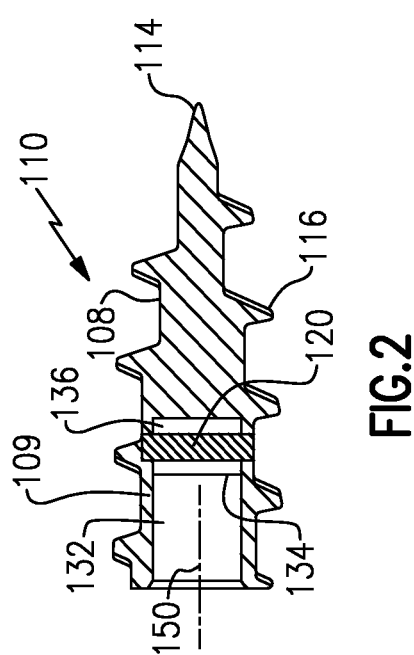

SUTURE ANCHOR

This application is a continuation of U.S. patent application Ser. No. 14/155,556 filed on Jan. 15, 2014, which is a continuation of U.S. patent application Ser. No. 14/148,460 filed on Jan. 6, 2014, now U.S. Pat. No. 8,801,755 granted on Aug. 12, 2014, which is a continuation of U.S. patent application Ser. No. 13/933,575 filed on Jul. 2, 2013, now U.S. Pat. No. 8,623,052 granted on Jan. 7, 2014, which is a continuation of U.S. patent application Ser. No. 12/751,266, filed on Mar. 31, 2010, which is a continuation of U.S. patent application Ser. No. 11/097,172 filed on Apr. 4, 2005, now U.S. Pat. No. 8,343,186, granted on Jan. 1, 2013, which claims the benefit of U.S. Provisional Application No. 60/559,425, filed Apr. 6, 2004, the entire disclosure of which is incorporated by reference herein.

BACKGROUND

Technical Field

The present invention relates to an apparatus for anchoring surgical suture to bone. More specifically, the present invention relates to a fully threaded suture anchor provided with a transverse anchor pin for securing, within the anchor, one or more strands of suture to anchor the suture to bone during arthroscopic surgery.

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Pat. No. 5,964,783.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking.

SUMMARY

An illustrative embodiment of the suture anchor of the present invention overcomes the disadvantages of the prior art discussed above by providing a threaded suture anchor having a transverse anchor pin disposed inside the body of the suture anchor. The suture anchor is made of a biocompatible metal, preferably a titanium alloy.

The proximal end surface of the threaded suture anchor of the present invention is preferably smooth and rounded to minimize suture abrasion, while the distal portion of the anchor is tapered to an elongated point to enable the anchor to be self-tapping. The proximal end portion of the suture anchor body has a hexagonally shaped opening to accept a hexagonal drive head.

The internal transverse pin provides a support over which one or more strands of suture can be looped, such that the suture is secured in a recessed fashion within the anchor.

Advantageously, suture attached to the anchor through the transverse pin exits the suture anchor through a central bore in the anchor, which prevents suture abrasion by the wall of the bone tunnel into which the anchor is inserted.

An illustrative suture anchor assembly includes an anchor body having a distal end, a proximal end, an exterior surface, a length extending along a central longitudinal axis, and a passage. The passage extends along the longitudinal axis, at least partially along the length, and from an opening at the proximal end. An external helical thread extends around the passage. The anchor body fixes a rigid member against relative movement along the longitudinal axis. The rigid member has a first dimension parallel to the central longitudinal axis and a second dimension perpendicular to the longitudinal axis, the second dimension being longer than the first dimension. The rigid member extends across the passage between a first portion of the exterior surface and a second portion of the exterior surface. A suture including ends is received about the rigid member and extends out of the opening. A driver includes a cannula having a distal opening and a proximal opening. The driver engages the anchor body, and the ends of the suture extend out of the proximal opening.

Another illustrative suture anchor assembly includes an anchor body having a distal end, a proximal end, an exterior surface, a length extending along a central longitudinal axis, and an internal passage. The passage extends along the longitudinal axis, at least partially along the length, and from an opening at the proximal end. An external helical thread extends around the passage. The anchor body fixes a rigid member against relative movement along the longitudinal axis. The rigid member has a first dimension parallel to the central longitudinal axis and a second dimension perpendicular to the longitudinal axis, the second dimension being longer than the first dimension. The second dimension of the anchor body is associated with the rigid member and is measured between a first portion of the exterior surface and a second portion of the exterior surface. A suture including ends is received about the rigid member and extends out of the opening. A driver includes a cannula having a distal opening and a proximal opening. The driver engages the anchor body, and the ends of the suture extend out of the proximal opening.

Another illustrative embodiment of a suture anchor assembly includes an anchor having a proximal end, a distal end, a longitudinal axis, a first length, and an internal passage within the anchor. The internal passage begins at an opening in the proximal end and has a second length shorter than the first length. A support structure fixed longitudinally relative to the anchor extends across the internal passage and has a third length shorter than the second length. A suture within the internal passage is received about a distal surface of the support structure. A suture extends out of the opening in the proximal end. A driver includes a cannula having a distal opening and a proximal opening, and the suture is received within the cannula. A first end and the second end of the suture extend outside of the proximal opening, the driver having a drive surface near the distal opening that engages the anchor.

Other features and advantages of the present invention will become apparent from the following description of the invention, which refers to the accompanying drawings.

BRIEF DESCRIPTION OF THE DRAWINGS

FIG. 1 is a side elevational view of the suture anchor of the present invention.

FIG. 2 is a longitudinal sectional view of the suture anchor shown in FIG. 1 through the plane D-D indicated therein.

FIG. 3 is a proximal end view of the suture anchor of FIG. 1.

FIG. 7 is a cross section of the suture anchor of FIG. 3.

DETAILED DESCRIPTION

Figure 4:
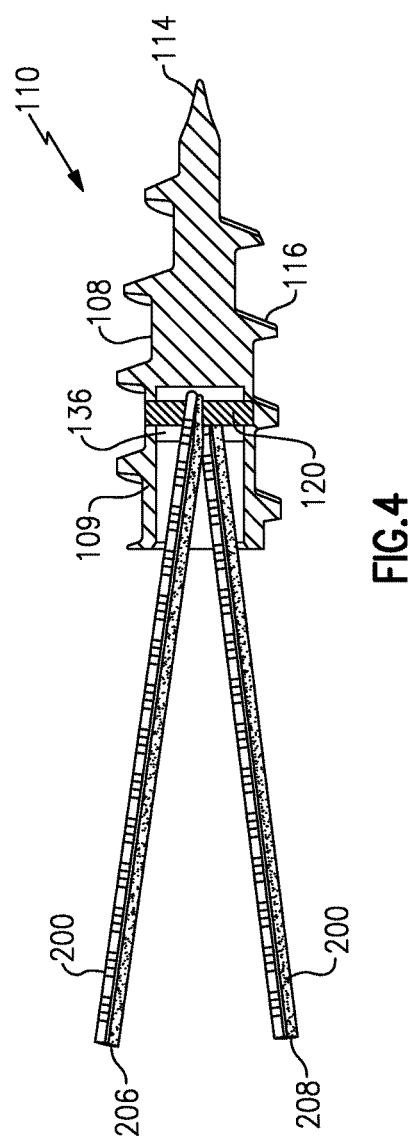
FIG. 4 is a cross sectional view of the suture anchor of FIG. 1 showing a suture looped over the transverse anchor pin.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

FIG. 1 illustrates a suture anchor according to a first preferred embodiment of the present invention, indicated generally by reference numeral 110. In the preferred embodiment, body 108 of anchor 110 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16°. The relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about five flights of thread, with the angle of the threads and other configurations of the anchor being similar to the suture anchor of U.S. Pat. No. 6,511,499, the disclosure of which is hereby incorporated by reference in its entirety.

As can be seen more clearly with reference to FIG. 2, the proximal end portion of the anchor has a hexagonally shaped bore 132 having an opening 122 at the proximal end of anchor body 108 and extending into the anchor body approximately one-third of the length thereof. Prior art anchors have sharp edges around the drive opening, which is problematic in that sutures passing through the central opening at the proximal end of the anchor can be abraded by the sharp edges, thereby compromising the strength of the sutures. The hexagonally shaped bore 132 includes at least two internal faces (not numbered). The two internal faces intersect obliquely relative to each other. In one example, there are six internal planar faces. In the suture anchor of the present invention, the peripheral edges defining hexagonally shaped opening 122 is smooth and rounded outwardly with no sharp edges. Preferably, the opening 122 forms a slight lip curving around the diameter of the bore 132. Thus, sutures threaded through the anchor 110, as will be discussed below, will not become frayed upon being pressed or rubbed against the anchor at the proximal opening 122.

A cylindrical bore 136 having a diameter corresponding to that of the hexagonally shaped bore 132 extends from the distal end of the hexagonally shaped bore 132 to a position roughly halfway along the length of anchor body 108. The transition between hexagonally shaped bore 132 and cylindrical bore 136 forms an annular shoulder 134, against which the distal end of a hex driver 202 abuts when inserted into the hexagonally shaped bore 132 to drive the anchor into bone. A wall 109 surrounds the cylindrical bore 136 and the hexagonal shaped bore 132, as shown in FIG. 2.

Two longitudinal, diametrically opposite apertures 118 are formed in anchor body 108, the apertures 118 supporting a metal transverse anchor pin 120 which extends across cylindrical bore 136.

As can be seen in FIGS. 1, 2 and 4, apertures 118 extend through and interrupt the threads 116 around anchor body 108 at approximately one-third of the length of the anchor body from the distal end thereof. One or more sutures 200 are secured to the anchor by looping the suture(s) around metal anchor pin 120 as shown in FIG. 4 and FIG. 7. Although the metal anchor pin 120 is illustrated in FIGS. 2 and 4 as oriented transverse to longitudinal axis 150 of the anchor body 108, the metal anchor pin 120 may form any angle with the longitudinal axis 150 and, thus, the invention is not limited to metal anchor pin 120 forming an angle of about ninety degrees with the longitudinal axis 150 of the anchor body 108.

Preferably, suture anchor 110 is formed of a hard biocompatible metal, such as a titanium alloy, but can be made of biocompatible materials other than metal. The suture secured to the anchor may be FiberWire suture, sold by Arthrex, Inc. of Naples, Ha.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is cast in a die, with the bores, passageways and apertures described above either being formed during the casting process or formed afterwards. If necessary, the distal tip 114 of the anchor 110 is trimmed to the desired length and the surfaces of the anchor are polished to the desired finish.

As mentioned above, the suture anchor of the present invention may be installed in the bone without the need to pre-drill a hole in the bone. The suture anchor is installed using a driver having a shaft having a hexagonal cross-section for at least a length equal to the length of the hexagonal bore 132 from proximal opening 122 to the shoulder 134 inside the anchor 110. The driver has a cannula extending through the entire length thereof, with openings at the proximal and distal ends thereof. Of course, the outer diameter of the hexagonal shaft is sized to fit inside the hexagonal bore in the anchor so as to be enabled to drive the same.

Figure 5:
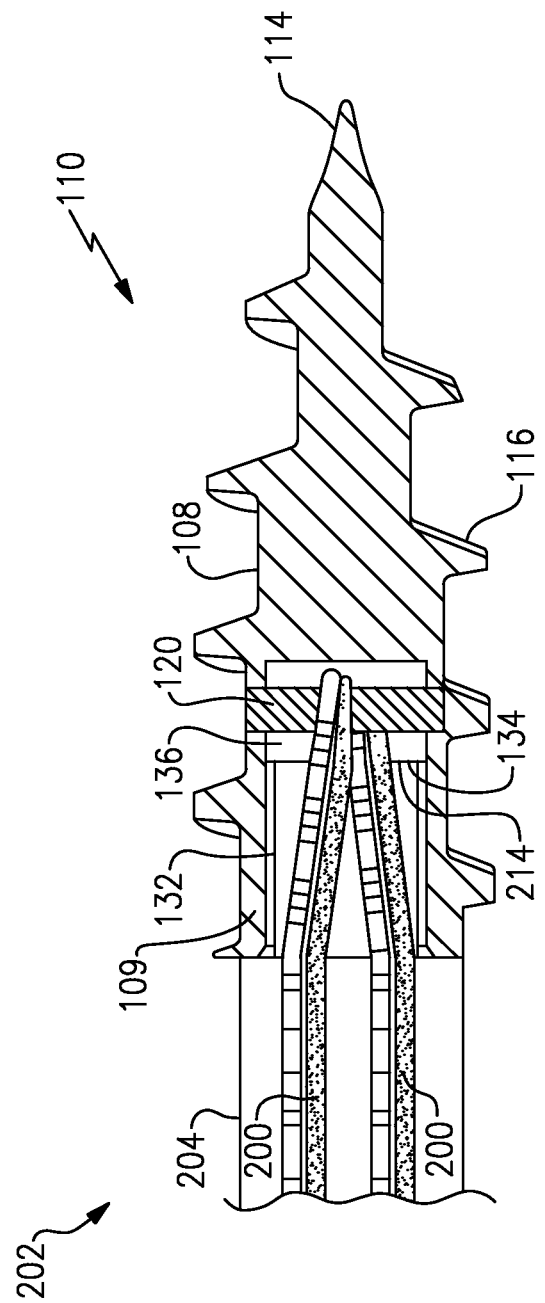
FIG. 5 is a cross sectional view of the suture anchor of FIG. 1 showing a portion of a hex driver inserted into a hexagonally shaped bore.
Figure 6:
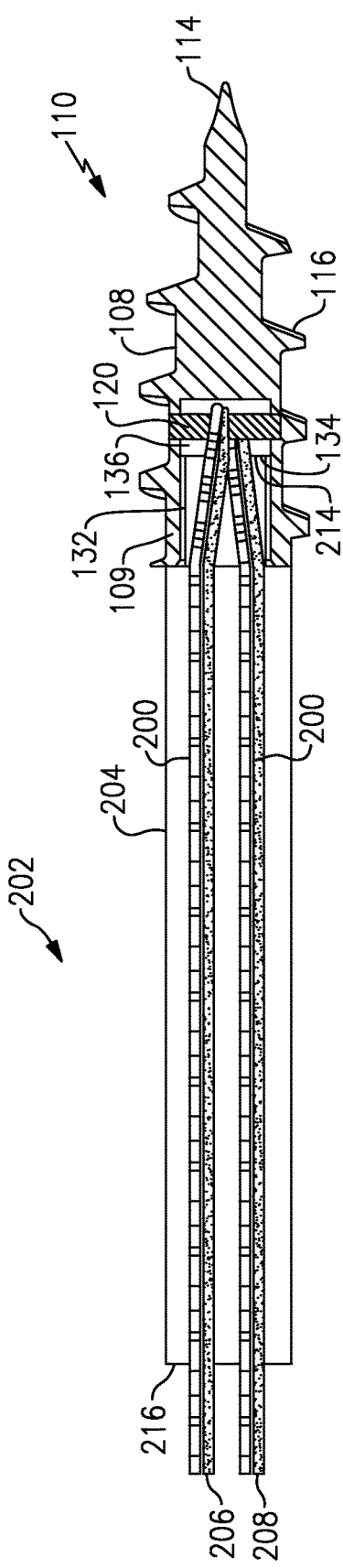
FIG. 6 is a cross sectional view of the suture anchor of FIG. 1 showing more of the hex driver inserted into a hexagonally shaped bore.

As shown in FIGS. 5 and 6, with the desired number of suture strands 200 threaded around the anchor pin 120 in the suture anchor 110, the ends 206 and 208 of the suture strands 200 are threaded through the cannula 204 in the hex driver 202 from the distal end thereof and extend from the proximal opening 216 thereof. The distal end 214 of the hex driver 202 is inserted into the proximal end of the anchor 110. With the distal end of the hex driver 202 abutting the shoulder 134 and the anchor 110 positioned at the location at which it is to be installed, the hex driver 202 is rotated to drive the anchor 110 into the bone until the proximal surface of the anchor 110 is flush with the surface of the bone.

Since it is not necessary for the proximal end of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor assembly comprising:
an anchor body including a central longitudinal axis, a proximal end, a distal end, a passage extending along the central longitudinal axis from an opening at the proximal end of the anchor body through at least a portion of a length of the anchor body, and a helical thread that defines a perimeter at least around the proximal end of the anchor body, wherein at least a portion of the passage has a first wall portion and a second wall portion;
a rigid support extending across the passage, wherein the rigid support has a first portion and a second portion spaced from the first portion, and the first portion is attached to the first wall portion of the anchor body and the second portion is attached to the second wall portion of the anchor body;
at least one suture strand having a suture length threaded into the passage, supported by the rigid support, and threaded past the proximal end of the anchor body, wherein the rigid support is spaced axially away from the opening at the proximal end along the central longitudinal axis, and the at least one suture strand extends out of the opening at the proximal end of the anchor body; and
a driver including a shaft having a shaft length, wherein the shaft engages the anchor body, and the suture length of the at least one suture strand is greater than the shaft length of the shaft.

2. The suture anchor assembly as recited in claim 1, wherein the anchor body and the rigid support are made of the same material.

3. The suture anchor assembly as recited in claim 1, wherein the driver has a first planar face and a second planar face, and the first planar face and the second planar face of the driver engage the first wall portion and the second wall portion, respectively, of the passage of the anchor body.

4. The suture anchor assembly as recited in claim 1, wherein the first wall portion and the second wall portion of the passage are located between the opening at the proximal end and the rigid support.

5. The suture anchor assembly as recited in claim 1, wherein the helical thread extends around at least a portion of the length of the anchor body.

6. The suture anchor assembly as recited in claim 1, wherein the passage at the proximal end of the anchor body is an internal passage.

7. A suture anchor assembly comprising:
an anchor body including a distal end, a proximal end, a length extending along a central longitudinal axis of the anchor body, a passage defined at least partially by a first interior surface spaced opposite to a second interior surface, and an exteriorly facing helical thread extending around the passage from the proximal end to a location near the distal end, wherein the passage extends about the central longitudinal axis, the passage extends from an opening located at the proximal end of the anchor body, and the passage extends at least partially along the length of the anchor body;
a rigid support fixed by the anchor body against relative movement along the central longitudinal axis of the anchor body, wherein the rigid support is attached to the first interior surface and to the second interior surface of the passage, and the rigid support is spaced axially away from the opening at the proximal end along the central longitudinal axis;

at least one tissue securing suture supported by the rigid support, wherein the at least one tissue securing suture includes a first end and a second end that extend out of the opening located at the proximal end of the anchor body; and a driver having a cannula, wherein the cannula has a distal opening and a proximal opening, the driver engaging the anchor body through at least a portion of the passage, and the first end and the second end of the at least one tissue securing suture extend out of the proximal opening of the cannula.

8. The suture anchor assembly as recited in claim 7, wherein the helical thread defines a perimeter that encircles the proximal end of the anchor body.

9. The suture anchor assembly as recited in claim 7, wherein the helical thread surrounds an entirety of the passage.

10. The suture anchor assembly as recited in claim 7, wherein the rigid support extends through the first interior surface and the second interior surface of the passage of the anchor body.

11. The suture anchor assembly as recited in claim 7, wherein the at least one tissue securing suture is received about a leading distal surface of the rigid support, and the leading distal surface extends across the central longitudinal axis of the anchor body.

12. The suture anchor assembly as recited in claim 7, wherein the driver has a first planar face and a second planar face, and the first planar face and the second planar face of the driver engages the first interior surface and the second interior surface, respectively, of the passage of the anchor body.

13. The suture anchor assembly as recited in claim 7, wherein the passage in an internal passage.

14. The suture anchor assembly as recited in claim 7, wherein the anchor body and the rigid support are made of the same material.

15. A suture anchor assembly comprising:
an anchor body including a distal end, a proximal end, a length extending along a central longitudinal axis of the anchor body, a passage defined at least partially by a first interior surface spaced opposite to a second interior surface, an anchor stop, and an exterior helical thread extending around at least a portion of the passage, wherein the passage surrounds the central longitudinal axis, the passage extends from an opening located at the proximal end of the anchor body, and the passage extends at least partially along the length of the anchor body;

a rigid support fixed by the anchor body against relative movement along the central longitudinal axis of the anchor body, wherein the rigid support branches from the first interior surface and the second interior surface of the passage, and the rigid support is spaced axially away from the opening at the proximal end along the central longitudinal axis;

at least one tissue securing suture having a suture length and supported by the rigid support, wherein the at least one tissue securing suture includes a first end and a second end that extend out of the opening located at the proximal end of the anchor body; and a driver having a cannula and a drive stop, wherein the cannula has a distal opening and a proximal opening, the driver engaging the anchor body through at least a portion of the passage, the first end and the second end of the at least one tissue securing suture extend out of the proximal opening of the cannula, and the drive stop and the anchor stop abut along the central longitudinal axis of the anchor body to stop movement of the shaft into the passage of the anchor body.

16. The suture anchor assembly as recited in claim 15, wherein the anchor stop is located inside the anchor body.

17. The suture anchor assembly as recited in claim 15, wherein the anchor stop is located in the passage of the anchor body.

18. The suture anchor assembly as recited in claim 15, wherein a portion of the at least one tissue securing suture that is received inside the passage is surrounded by the helical thread of the anchor body.

19. The suture anchor assembly as recited in claim 15, wherein the driver has a first planar face and a second planar face, and the first planar face and the second planar face of the driver engage the first interior surface and the second interior surface, respectively, of the passage of the anchor body.

20. The suture anchor assembly as recited in claim 15, wherein the anchor body and the rigid support are made of the same material.

21. The suture anchor assembly as recited in claim 15, wherein the passage is an internal passage.

22. The suture anchor assembly as recited in claim 15, wherein the at least one tissue securing suture is received about a leading distal surface of the rigid support, and the leading distal surface extends across the central longitudinal axis of the anchor body.

23. A suture anchor assembly comprising:
an anchor body including a distal end, a proximal end, a length extending along a central longitudinal axis of the anchor body, a passage defined at least partially by a first interior planar surface spaced opposite to a second interior planar surface, an exterior surface, and an exterior helical thread extending around at least a portion of the passage, wherein the passage extends about the central longitudinal axis, the passage extends from an opening located at the proximal end of the anchor body, and the passage extends at least partially along the length of the anchor body;

a rigid support fixed by the anchor body against relative movement along the central longitudinal axis of the anchor body, wherein the rigid support is secured to the first interior planar surface and to the second interior planar surface of the passage, and the rigid support is spaced axially away from the opening at the proximal end along the central longitudinal axis;

at least one tissue securing suture supported by the rigid support, wherein the at least one tissue securing suture includes a first end and a second end that extend out of the opening located at the proximal end of the anchor body; and a driver having a cannula, wherein the cannula has a distal opening and a proximal opening, the driver engaging the anchor body through at least a portion of the passage, and the first end and the second end of the at least one tissue securing suture extend out of the proximal opening of the cannula.

24. The suture anchor assembly as recited in claim 23, wherein the rigid support is secured in a fixed longitudinal position by the first interior planar surface and the second interior planar surface of the passage of the anchor body.

25. The suture anchor assembly as recited in claim 23, wherein a portion of the at least one tissue securing suture that is received inside the passage is encompassed by the exterior surface of the anchor body.

26. The suture anchor assembly as recited in claim 23, wherein the first interior planar surface and the second interior planar surface are both generally parallel to the central longitudinal axis of the anchor body.

27. The suture anchor assembly as recited in claim 23, wherein the first interior planar surface and the second interior planar surface are generally parallel relative to each other.

28. The suture anchor assembly as recited in claim 23, wherein an intersection of the first interior planar surface and the second interior planar surface defines a line.

29. The suture anchor assembly as recited in claim 23, wherein the passage at the proximal end of the anchor body is an internal passage.

30. A suture anchor comprising:
   an anchor body including a distal end, a proximal end, a length extending along a central longitudinal axis of the anchor body, an exterior surface, a passage defined at least partially by a first interior surface spaced opposite to a second interior surface, and an exterior helical thread surrounding at least a portion of the passage, wherein the passage extends about the central longitudinal axis, the passage extends from an opening located at the proximal end of the anchor body, and the passage extends at least partially along the length of the anchor body;
   a rigid support fixed by the anchor body against relative movement along the central longitudinal axis of the anchor body, wherein the rigid support is attached to the first interior surface and to the second interior surface of the passage, the rigid support is spaced axially away from the opening at the proximal end along the central longitudinal axis, and the rigid support is located in the passage and surrounded by the helical thread;
   at least one tissue securing suture having a suture length and supported by the rigid support, wherein at least a portion of at least one tissue securing suture is disposed in the passage between the rigid support and the opening at the proximal end and surrounded by the helical thread, the at least a portion of the at least one tissue securing suture that is disposed in the passage is surrounded by the exterior surface of the anchor body, and the at least one tissue securing suture includes a first end and a second end that extend out of the opening located at the proximal end of the anchor body; and
   a driver having a cannula, wherein the cannula has a distal opening and a proximal opening, the driver engaging the anchor body through at least a portion of the passage, and wherein the first end and the second end of the at least one tissue securing suture extend out of the proximal opening of the cannula.

31. The suture anchor assembly as recited in claim 30, wherein the rigid support is secured at the fixed longitudinal position at an interface between the rigid support and the first interior surface and the second interior surface of the passage.

32. The suture anchor assembly as recited in claim 30, wherein the rigid support is secured in the fixed longitudinal position by the first interior surface and the second interior surface of the passage of the anchor body.

33. The suture anchor assembly as recited in claim 30, wherein the external helical thread extends to the proximal end of the anchor body.

34. The suture anchor assembly as recited in claim 30, wherein the driver engages the first interior surface and the second interior surface of the passage.

35. The suture anchor assembly as recited in claim 30, wherein the passage at the proximal end of the anchor body is an internal passage.

* * * * *

UNITED STATES PATENT AND TRADEMARK OFFICE
CERTIFICATE OF CORRECTION

PATENT NO. : 9,622,739 B2
APPLICATION NO. : 14/487459
DATED : April 18, 2017
INVENTOR(S) : Peter J. Dreyfuss and William C. Benavitz It is certified that error appears in the above-identified patent and that said Letters Patent is hereby corrected as shown below:

In the Claims

In Claim 15, Column 8, Line 2; after "movement of" replace "the shaft" with --the cannula--

In Claim 30, Column 9, Line 20; before "helical" replace "exterior" with --external--

In Claim 31, Column 10, Line 18; before "fixed longitudinal" replace "the" with --a--

In Claim 32, Column 10, Line 23; before "fixed longitudinal" replace "the" with --a--

Signed and Sealed this
Twenty-ninth Day of August, 2017

Joseph Matal
*Performing the Functions and Duties of the
Under Secretary of Commerce for Intellectual Property and
Director of the United States Patent and Trademark Office*